United States Patent
Andrews et al.

(10) Patent No.: US 7,129,357 B2
(45) Date of Patent: Oct. 31, 2006

(54) SYNTHESIS OF QUINOLINE 5-CARBOXAMIDES USEFUL FOR THE PREPARATION OF PDE IV INHIBITORS

(75) Inventors: David R. Andrews, Maplewood, NJ (US); Suhan Tang, Plainsboro, NJ (US); Wenxue Wu, Princeton Junction, NJ (US); Sami Y. Kalliney, Chatham, NJ (US); Anantha Sudhakar, Freemont, CA (US); Christopher Nielsen, Westfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 142 days.

(21) Appl. No.: 10/939,740

(22) Filed: Sep. 13, 2004

(65) Prior Publication Data

US 2005/0124655 A1    Jun. 9, 2005

Related U.S. Application Data

(60) Provisional application No. 60/503,108, filed on Sep. 15, 2003.

(51) Int. Cl.
*C07D 215/20* (2006.01)
*C07D 215/38* (2006.01)

(52) U.S. Cl. .......................... 546/169; 546/170; 560/23
(58) Field of Classification Search ................. 560/23; 546/170, 169
See application file for complete search history.

(56) References Cited

U.S. PATENT DOCUMENTS 5,804,588 A    9/1998   Dyke et al.
6,410,559 B1 *  6/2002   Dyke et al. ................. 514/311

OTHER PUBLICATIONS

Cocco, MT et al 'Annulation of functionalized hexadienones as an efficient regioselective approach to N-aryl-2-(trifluoromethyl)—4-pyridinamines' CA 131:129877 (1999).*

Cottet, Fabrice, et al., "Recommendable Routes to Trifluoromethyl-Substituted Pyridine- and Quinolinecarboxylic Acids," *Eur. J. Org. Chem.* (2003) 1559-1568.
Billah, Motasim, et al., "8-Methoxyquinolines as PDE4 Inhibitors," *Bioorganic & Medicinal Chemistry Letters 12* (2002) 1617-1619.
Billah, Motasim, et al., "Synthesis and Profile of SCH351591, a Novel PDE4 Inhibitor," *Bioorganic & Medicinal Chemistry Letters* 12 (2002) 1621-1623.
Marull, Marc, et al., "Selective and Efficient Structural Elaboration of 2-(Trifluorormethyl)quinolinones," *Eur. J. Org. Chem.*(2003) 1576-1588.
International Search Report for PCT/US2004/029773—4 Pages.
M. Billah et al., 8-Methoxyquinolines as PDE4 Inhibitors, Bioorganic and Medicinal Chemistry Letters, vol. 12, 2002, pp. 1617-1619, XP002317027.
M. Billah et al., Synthesis and Profile of SCH351591, a Novel PDE4 Inhibitor Bioorganic and Medicinal Chemistry Letters, vol. 12, 2002, pp. 1621-1623, XP002317028.
M. Marull et al., Selective and Efficient Structural Elaboration of 2-(Trifluoromethyl) Quinolines, European J. of Org. Chem., vol. 2003, No. 8, pp. 1576-1588 XP002317029.
G. Jones et al., Chemistry of Heterocyclic Compounds, vol. 32(1), 1977, John Wiley & Sons, London, GB pp. 100-117 XP002317030.

* cited by examiner

*Primary Examiner*—Amélia A. Owens
(74) *Attorney, Agent, or Firm*—H. Eric Fischer; Palaiyur S. Kalyanaraman

(57) ABSTRACT

In one embodiment, the present application discloses a process for making the compound of the formula:

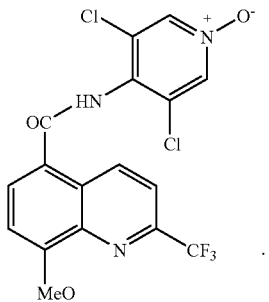

21 Claims, No Drawings

SYNTHESIS OF QUINOLINE 5-CARBOXAMIDES USEFUL FOR THE PREPARATION OF PDE IV INHIBITORS

This application claims priority from U.S. provisional patent application Ser. No. 60/503,108 filed Sep. 15, 2003.

FIELD OF THE INVENTION

This application discloses a novel process to synthesize certain substituted quinoline 5-carboxamides useful as phosphodiesterase IV ("PDE IV") inhibitors.

BACKGROUND OF THE INVENTION

PDE IV is present in all the major inflammatory cells including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. Non-selective PDE inhibitors, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with PDE inhibitors is apparent.

U.S. Pat. No. 5,804,588 discloses several quinoline 5-carboxamides as PDE IV inhibitors. A compound disclosed therein has the formula I:

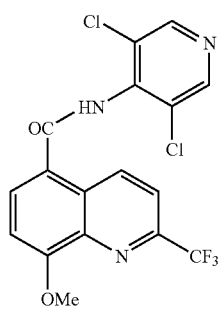

I

The N-oxide of the compound of formula I is the compound of formula II, which is disclosed in U.S. Pat. No. 6,410,559. The '559 patent additionally discloses a process to synthesize the compound of formula II and analogs.

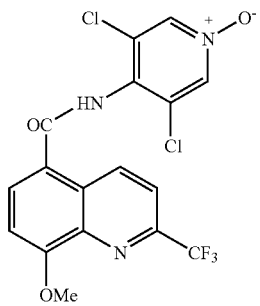

II

Furthermore, M. Billah et al, *Bioorg. & Medicinal Chem.*, (2002), 12, 1621–1623, disclose the compound of formula I as well as its N-oxide, the compound of formula II.

M. Billah et al, *Bioorg. & Medicinal Chem.*, (2002), 12, 1617–1619, describe a process to synthesize the compounds of formulas I and II. The synthesis which goes through the compound of formula III:

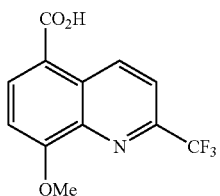

III involves several tedious steps and necessitates the use of expensive starting materials and the use of a palladium catalyst. Removal of the palladium catalyst is generally difficult as is known to those skilled in the art.

Attention is also drawn to M. Marull et al, *Eur. J. Org. Chem*, (2003), 1576–1588, and F. Cottet and M. Marull et al, *Eur. J. Org. Chem*, (2003), 1559–1568, respectively describing the synthesis of certain quinolinones and recommendable routes to trifluoromethyl-substituted quinoline carboxylic acids.

There remains a need for new, economical methods of making PDE IV inhibitors based on quinoline carboxamide structure. This invention provides a process to prepare such quinoline compounds carrying a trifluoromethyl group at the 2-position and having a substituent at the 8-position of the quinoline moiety.

SUMMARY OF THE INVENTION

In one embodiment, the present application discloses a process of making a quinoline 5-carboxamido compound of formula IV:

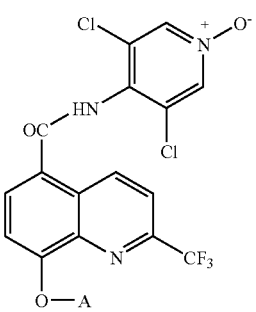

IV wherein A is selected from the group consisting of H, alkyl, cycloalkyl, heterocyclyl, —CF$_3$, aryl, and heteroaryl, said process comprising:

(1) reacting a compound of formula V with a compound of formula VI to yield a compound of formula VII:

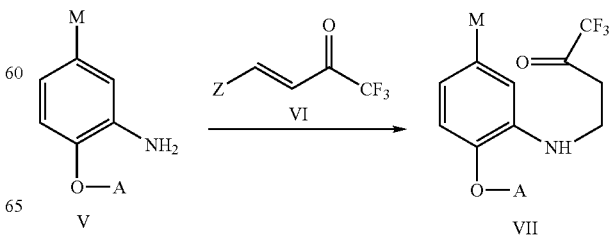

wherein
  A is defined above;
  M is —C(O)OH, or a group chemically convertible to —C(O)OH;
  Z is selected from the group consisting of halogen, —OR⁴, —NR⁵R⁶ and —SR⁷; and
  R⁴, R⁵, R⁶, and R⁷ can be the same or different with each being independently selected from the group consisting of H, alkyl, aryl, aralkyl, heteroaryl, cycloalkyl, and heterocyclyl, wherein each of said alkyl, aryl, aralkyl, heteroaryl, cycloalkyl, and heterocyclyl can be unsubstituted or optionally independently substituted with 1–4 W moieties, which can be the same or different, wherein W is selected from the group consisting of alkyl, halo, cycloalkyl, heterocyclyl, aryl and heteroaryl;

(2) cyclizing the compound of formula VII to a compound of formula VIII:

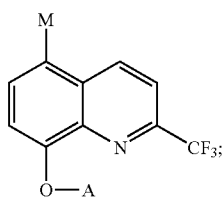

VIII (3) converting, when M is not —C(O)OH, the compound of formula VIII to a compound of formula IX:

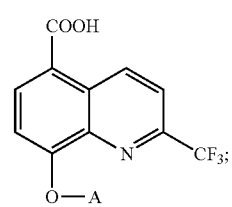

IX (If M is C(O)OH to begin with, step (3) doesn't apply since the compounds of Formulas VIII and IX will be the same in that case) and (4) reacting the compound of formula IX with a compound of formula X to yield the compound of formula IV:

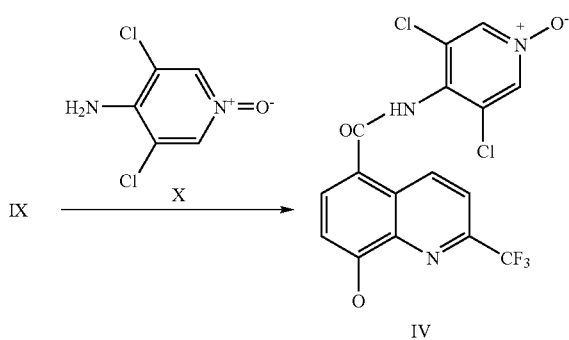

The term "chemically convertible" for the group M refers to moieties that are chemically convertible to —C(O)OH by synthetic processes known to those skilled in the art. (This is practiced in step 3) above.) Non-limiting examples of such "chemically convertible" groups for M in the present context include —Br, —Cl, —I, —CN, —C(O)OR, —C(O)NR¹R² and —C(O)SR³ wherein R is selected from the group consisting of alkyl, aryl, aralkyl, heteroaryl, cycloalkyl, and heterocyclyl, and R¹, R² and R³ can be the same or different, with each being independently selected from the group consisting of H, alkyl, aryl, aralkyl, heteroaryl, cycloalkyl, and heterocyclyl,
wherein each of the afore-mentioned alkyl, aryl, aralkyl, heteroaryl, cycloalkyl, and heterocyclyl can be unsubstituted or optionally independently substituted with 1–4 W moieties, which can be the same or different, wherein W is selected from the group consisting of alkyl, halo, cycloalkyl, heterocyclyl, aryl and heteroaryl. M can be —C(O)OH too as stated earlier.

The inventive process to make the compound of formula I has several advantages such as, for example, reduced reaction temperatures, economic starting materials, higher yield and purity.

DESCRIPTION OF THE INVENTION

In an embodiment, the present invention discloses a process for preparing a compound of formula IV.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)₂, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl, groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Alkylene" means a difunctional group obtained by removal of a hydrogen atom from an alkyl group that is defined above. Non-limiting examples of alkylene include methylene, ethylene and propylene.

"Aryl" (sometimes abbreviated "ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1–2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

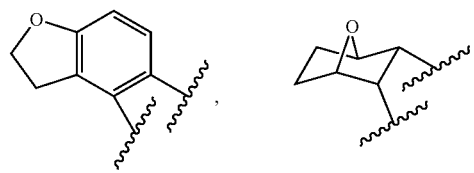

and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of about 5 to about 6 ring atoms. The arylcycloalkyl can be optionally substituted by one or more ring system substituents, wherein "ring system substituent" is as defined above. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The heteroarylcycloalkyl can be optionally substituted by one or more ring system substituents, wherein "ring system substituent" is as defined above. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like. The bond to the parent moiety is through a non-aromatic carbon atom.

"Cycloalkylheteroaryl" means a group derived from a fused beteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates.

Non-limiting examples of suitable solvates include ethanolates, methanolates, and the like. "Hydrate" is a solvate wherein the solvent molecule is $H_2O$.

The wavy line ~~~as a bond generally indicates a mixture of, or either of, the possible isomers, e.g., containing (R)- and (S)-stereochemistry. For example,

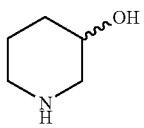

means containing both and

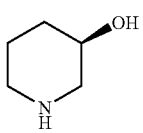 and 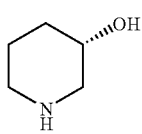

Lines drawn into the ring systems, such as, for example:

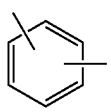

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

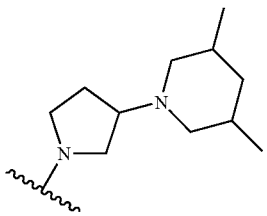

represents

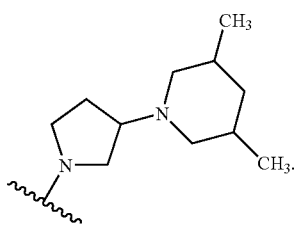

It should also be noted that any carbon or heteroatom with unsatisfied valences in the text, schemes, examples, structural formulae, and any Tables herein is assumed to have the hydrogen atom or atoms to satisfy the valences.

In one embodiment, the present invention discloses a process for preparing the compound of formula IV. The inventive process is schematically described in Scheme 1 below:

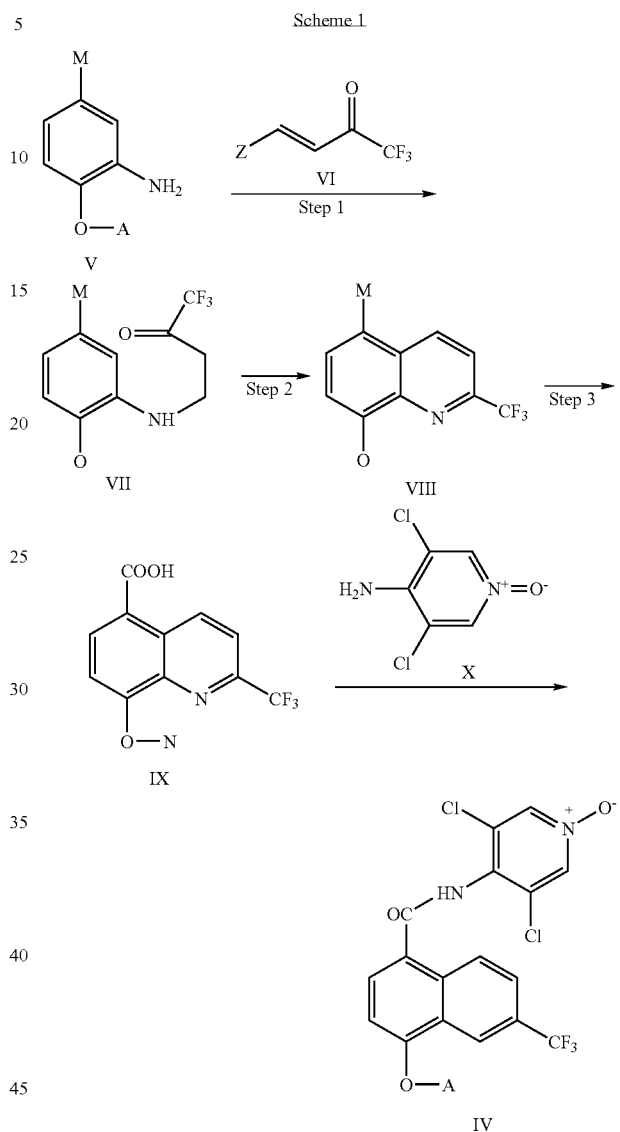

wherein A, M, and Z are defined above.

The synthesis of the compound of the formula XI:

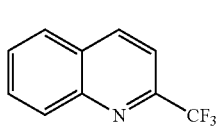

XI by cyclizing a triflated amine has been described by M. Schlosser et al, *Tetrahedron Letters*, (1997), 38, 8523–8526, and by H. Keller et al, *Tetrahedron*, (1996) 13, 4637–4644.

The various reaction steps outlined in the inventive processes of this application may additionally optionally contain one or more suitable solvents to facilitate the reaction. While the preferred reagents and reaction conditions for the various steps are described in detail in the Examples section, the following summarizes the details.

Step 1:

In step 1, a compound of formula VI is reacted with a compound of formula V to yield a compound of formula VII. The compound of formula VI may be commercially available, or it may be prepared prior to, or in situ during, the reaction of step 1. In an illustrative example, the compound of formula VI is 1,1,1-trilfuoro-4-ethoxybut-3-en-2one, which may be prepared, for example, by reacting trifluoroacetic anhydride and ethyl vinyl ether. 1,1,1-Trilfuoro-4-ethoxybut-3-en-2one may be reacted with the amine of formula V as follows. The amine is dissolved, dispersed, or otherwise suitably suspended in a suitable solvent and the enone of formula VI is added to it. The reaction mixture is stirred for a duration of about 30 minutes to until the reaction is complete, at a temperature ranging from about −20° C. to about the reflux temperature of the solvent, to yield the compound of formula VII. Non-limiting examples of suitable solvents include alcohol, hydrocarbon, ether, ketone, ester and mixtures thereof. Non-limiting examples of hydrocarbon solvents include pentane, hexane, heptane, benzene, xylene, toluene, and the like, and mixtures thereof. Non-limiting examples of alcohol solvents include methanol, ethanol, propanol, butanol, and the like, and mixtures thereof. Preferred solvents include alcohol solvents, more preferably methyl alcohol or ethyl alcohol. The compound of formula VI can be used generally from about 0.2 molar equivalents to about 1.2 molar equivalents with respect to the compound of formula V, preferably from about 0.8 molar equivalents to about 1.2 molar equivalents, and more preferably from about 1 molar equivalents to about 1.2 molar equivalents. The solvent may be used generally in about 1–20 volume equivalents with respect to the compound of formula V, preferably in about 2–15 volume equivalents, and more preferably in about 2–5 volume equivalents. The product of formula VII may be isolated by procedures well known to those skilled in the art.

The compound of formula VII may be prepared by an alternate process too from a compound of formula V. Thus, the compound of formula VI in step 1 can be substituted with the compound of formula A below wherein X is selected from the group consisting of Cl, —NR$^1$R$^2$, —OP(O)Cl$_2$, —OSO$_2$R$^3$ and —OP(O)(OR$^4$)$_2$, and wherein R$^1$, R$^2$, R$^3$ and R$^4$ are as defined above.

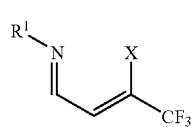

A

This alternate process can yield the compound of formula B below:

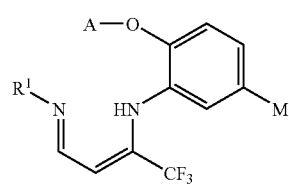

B

The compound of formula B can be cyclized under the conditions described below in Step 2 to yield the compound of formula VIII.

Step 2:

The compound of formula VII can be cyclized to form a compound of formula VIII, in an illustrative procedure as follows: to a solution (or suspension or suitable dispersion) of the compound of formula VII in a suitable solvent is added a suitable dehydrating agent. Non-limiting examples of suitable solvents include ether, hydrocarbon, nitrile, ester, chlorinated solvents and mixtures thereof. Non-limiting examples of hydrocarbon solvents include pentane, hexane, heptane, benzene, xylene, toluene, and the like, or mixtures thereof. Non-limiting examples of nitrile solvents include propionitrile, acetonitrile, and the like, or mixtures thereof. Non-limiting examples of ester solvents include ethyl acetate, isopropyl acetate, and the like, or mixtures thereof. Non-limiting examples of chlorinated solvents include methylene chloride, 1,2-dichloroethane, chlorobenzene, and the like, or mixtures thereof. Non-limiting examples of ether solvents include 1,2-dimethoxyethane, tetrahydrofuran (THF), diglyme and the like, or mixtures thereof. Preferred solvents include acetonitrile and ethyl acetate, more preferably acetonitrile. Non-limiting examples of dehydrating agents include POCl$_3$, PCl$_3$, trifluoroacetic anhydride ("Tf$_2$O"), Ms$_2$O (methanesulfonic anhydride), PCl$_5$ and P$_2$O$_5$. Cyclization of imines using Tf$_2$O has been described by 1. Baraznenok et al, *Eur. J. Org. Chem.*, (1999), 937–941. Preferred dehydrating agents include POCl$_3$, Tf$_2$O and Ms$_2$O, more preferably POCl$_3$. The solution is then agitated for about 30 minutes or until the reaction is complete at a temperature ranging from about room temperature to about the reflux temperature of the solvent, preferably from about 60° C. to about the reflux temperature, more preferably at about the reflux temperature. In a preferred embodiment, the compound of formula VI is added to the reaction mixture and the reaction mixture is refluxed for another 12 hours. The reaction may be worked up by procedures well known to those skilled in the art to obtain the compound of formula IV. POCl$_3$ can be used from at least about 0.2 molar equivalents with respect to the compound of formula VII, preferably at least about 0.8 molar equivalents, and more preferably from about 1.0 to about 1.2 molar equivalents.

Alternatively, reaction steps 1 and 2 may be combined as follows: the compound of formula VI (where Z is now —NHR) can be treated with a dehydrating agent, followed by the addition of the compound of formula V, to yield the compound of formula VIII:

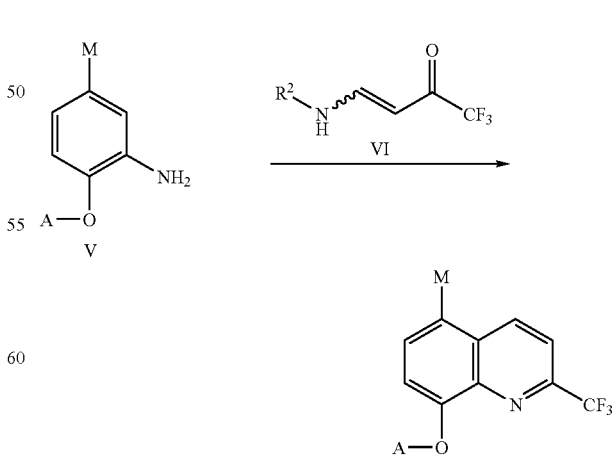

Step 3:

To a mixture of the compound of formula VIII, wherein M is C(O)OH, in a suitable solvent at room temperature, is added an aqueous solution of a suitable base. (If M is Br, Cl, I, CN, C(O)NR$^1$R$^2$, or C(O)SR$^3$, (and not —C(O)OH), the compound of formula VIII can then be converted to the compound of formula IX by methods familiar to those skilled in the art, or in the alternative, the compound of formula VIII where M is a functional group convertible to —C(O)OH such as, for example, Br, Cl, I, CN, C(O)NR$^1$R$^2$, or C(O)SR$^3$, can first be converted to the compound of formula VIII where M is —C(O)OR by suitable processes, and then that compound may be reacted as described above.) Non-limiting examples of suitable solvents include ether, alcohol, nitrile and the like, and mixtures thereof. Non-limiting examples of ether solvents include THF, tert-butyl methyl ether ("TBME"), diethyl ether, diglyme, and the like, and mixtures thereof. Non-limiting examples of nitrile solvents include propionitrile, acetonitrile, and the like, and mixtures thereof. Non-limiting examples of alcohol solvents include methanol, ethanol, isopropanol, and the like, and mixtures thereof. Preferred solvents include ether solvents, more preferably THF. Non-limiting examples of suitable bases include sodium carbonate, potassium carbonate, sodium bicarbonate, potassium bicarbonate, sodium hydroxide, potassium hydroxide, and lithium hydroxide, preferably sodium hydroxide, potassium hydroxide, lithium hydroxide, and the like, and mixtures thereof. Preferred bases include sodium hydroxide and lithium hydroxide. The reaction mixture is stirred at a temperature ranging from about room temperature to about the reflux temperature, preferably from about 60° C. to about the reflux temperature, more preferably at about the reflux temperature, for about 2 hours or until the reaction is complete. The solution is then acidified with an organic or inorganic acid such as, for example, ammonium sulfate, ammonium nitrate, ammonium chloride, trifluoroacetic acid (TFAA), H$_2$SO$_4$, HCl, H$_3$PO$_4$, citric acid, mesyl chloride, paratoluenesulfonic acid, paratoluenesulfonic acid pyridinium salt, an alkyl sulfonic acid, and the like, or mixtures thereof, to yield the compound of formula IX. Preferred acid is HCl. The base can be used generally from at least about 0.2 molar equivalents with respect to the compound of formula VIII, preferably at least about 0.8 molar equivalents, and more preferably from about 1.0 to about 1.2 molar equivalents.

Step 4:

The compound of formula IX from step 3 in a suitable solvent is mixed with an acid chloride such as, for example, SOCl$_2$ or oxalyl chloride, preferably SOCl$_2$ to form the corresponding acid chloride. Non-limiting examples of suitable solvents include acetonitrile, methylene chloride, propionitrile, DMF, N-methyl-pyrrolidinone (NMP), THF, and the like, or mixtures thereof, preferably acetonitrile. The reaction mixture is performed at about room temperature to about the reflux temperature, preferably from about 30° C. to about 60° C., more preferably from about 40° C. to about 45° C. for a time ranging from about 30 minutes to about 6 hours, preferably from about 45 minutes to about 2 hours, more preferably for about 1 hour.

Separately, the compound of formula X (commercially available or separately prepared as described, for example, in the EXAMPLES section) and a suitable base are mixed in a suitable solvent at about the room temperature to about 60° C., for about 1 hour or until the reaction is complete. Non-limiting examples of suitable solvents include nitriles, hydrocarbons, chlorinated hydrocarbons, amides, ethers and the like and mixtures thereof. Examples of solvents include acetonitrile, methylene chloride, propionitrile, DMF, NMP, THF, and the like, and mixtures thereof. Preferred solvent is acetonitrile, DMF or mixtures thereof. Non-limiting examples of suitable bases include sodium hydride, sodium methoxide, potassium methoxide, sodium carbonate, potassium carbonate, sodium hydride, sodium bicarbonate, potassium bicarbonate, sodium hydroxide, potassium hydroxide, lithium hydroxide, and the like, and mixtures thereof. Preferred bases include sodium hydride, sodium methoxide, potassium methoxide, sodium hydroxide, potassium hydroxide and lithium hydroxide, more preferably lithium hydroxide. To the resulting mixture is added the above-described solution or mixture containing the acid chloride of compound of formula IX. The reaction mixture is then stirred for about 30 minutes or until the reaction is complete to yield the compound of formula IV. The reaction is performed at about 10° C. to about 80° C., preferably at about 15° C. to about 60° C. and more preferably at about 20° C. to about 40° C. The compound of formula X can be used generally in at least about 1.0 molar equivalents with respect to the compound of formula IX, preferably at least about 1.5 molar equivalents, and more preferably from about 1.8 to about 2.2 molar equivalents.

The product (the compound of formula IV) is isolated by acidification of the reaction mixture with a suitable acid selected from the group consisting of acetic acid, HCl, H$_2$SO$_4$ and the like and mixtures thereof, at about –10° C. to about 40° C. Preferred acid is HCl.

The products of the various steps in the reaction schemes described herein may be isolated and purified by conventional techniques such as, for example, filtration, recrystallization, solvent extraction, distillation, precipitation, sublimation and the like, well known to those skilled in the art. The products may be analyzed and/or checked for purity by conventional methods well known to those skilled in the art such as, for example, thin layer chromatography, NMR, HPLC, melting point, mass spectral analysis, elemental analysis and the like.

The following nonlimiting EXAMPLES are provided in order to further illustrate the present invention. The reactions have been described with A being methyl and M being methoxycarbonyl in the formulas; however, it will be apparent to those skilled in the art that such a description is for illustrative purposes only and not limitative in any respect. Many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations have the stated meanings in the Examples below:

Hz=Hertz
MHz=Megahertz
mL=milliliter
NMR=nuclear magnetic resonance spectroscopy
DME=dimethyl ether
DMSO=dimethylsulfoxide
EDCl=1-(3-Diemthylaminopropyl)-3-ethylcarbodiimide hydrochloride
EtOAc=ethyl acetate
THF=tetrahydrofuran The compounds in the following examples reflect the compounds in the various formulas where A is methyl and M is methoxycarbonyl.

Example 1

Preparation of the Compound of Formula VII

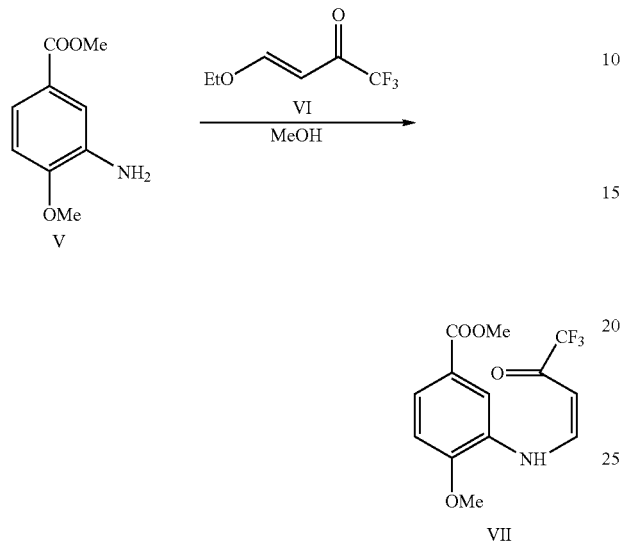

Example 2

Preparation of the Compound of Formula VIII

Cyclization when Z=ethoxy:

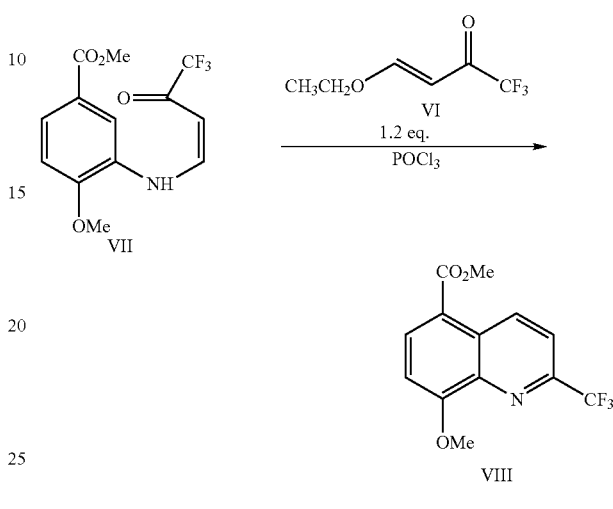

To a solution of methyl 4-methoxy-3-{[(E)-4-trifluoromethyl-3-oxo-1-butenyl]amino} benzoate (the ester of formula VII, 760 g, 2.5 mol) in 6 L $CH_3CN$ at 50° C., $POCl_3$ (282 mL, 3.0 mol) was added. The solution was then heated to reflux for about 7 hours. Then the enone (i) (213 g, 1.25 mol) was added. After refluxing for another 12 hours, the solvent was removed. The residue was then dissolved in 5 L of EtOAc and 700 mL of $H_2O$. The resulting solution was poured into a solution of $K_2CO_3$ (1200 g) in 6 L of $H_2O$. After stirring for 20 minutes at room temperature, the layers were separated. Removal of the solvent from the organic layer followed by agitating in 2 L MeOH gave the desired compound VIII, methyl 8-methoxy-2-trifluoromethyl-5-quinolinecarboxylate, (420 g, 59% yield). $^1$H NMR (400 MHz, $CDCl_3$) δ 4.01 (s, 3H), 4.18 (s, 3H), 7.13 (d, J=8.4 Hz, 1H), 7.90 (d, J=8.8 Hz, 1H), 8.46 (d, J=8.4 Hz, 1H), 9.74. (d, J=8.8 Hz, 1H).

$^{13}$C NMR (100 MHz, $CDCl_3$) δ 52.50, 56.99, 107.58, 117.72, 117.98, 121.82 (q), 129.67, 135.08, 137.33, 139.32, 146.96 (q).

Table I lists unoptimized yields for the compound of formula VIII from reactions conducted in various solvents using substantially the same procedure as described in step 2.

Preparation of the Enone (Formula VI)

To a solution of ethyl vinyl ether (199 mL) in 500 mL of $CH_2Cl_2$, pyridine (180 mL) was added. Then a solution of trifluoroacetic anhydride (438 g) in 250 mL of $CH_2Cl_2$ was added at 0° C. After stirring at room temperature for 30 minutes, the solution was poured into 200 mL of $H_2O$. The layers were separated and the aqueous layer was extracted again with 200 mL $CH_2Cl_2$. The organic layers were combined, washed with $H_2O$ and dried over $MgSO_4$. Removal of solvent then gave the crude enone VI, 1,1,1-trifluoro-4-ethoxybut-3-en-2-one, (292 g), which was used in the next step without further purification.

$^1$H NMR (400 MHz, $CDCl_3$) δ 1.42 (t, J=7.0 Hz, 3H), 4.12 (q, J=7.0 Hz, 2H), 5.86 (d, J=12.4 Hz, 1H), 7.92 (d, J=12.4 Hz, 1H).

Preparation of the Compound of Formula VII:

To a solution of methyl-3-amino-4-methoxybenzoate (a compound of formula II, available from Indofine Chemical Company, Inc., Somerset, N.J.), (315 g, 1.74 mol) in 1 L MeOH, the crude enone VI (350 g, ~2.09 mol) was added. The reaction was stirred at room temperature for 30 minutes. After cooling to 0° C. for 1 hour, the solid was filtered and dried under vacuum to give the desired compound of formula VII, methyl 4-methoxy-3-{[(E)-4-trifluoromethyl-3-oxo-1-butenyl]amino} benzoate, (500 g, 95% yield) as a yellow solid.

$^1$H NMR (400 MHz, $CDCl_3$) δ 3.94 (s, 3H), 4.04 (s, 3H), 5.74 (d, J=8.0 Hz, 1H), 7.00 (d, J=8.8 Hz, 1H), 7.79 (dd, J=13.2, 8.0 Hz, 1H), 7.87 (dd, J=8.8, 2.0 Hz, 1H), 7.92 (d, J=2.0 Hz, 1H), 11.01 (br, 1H).

TABLE I

| Solvent | Yield |
|---|---|
| Chlorobenzene | 46% |
| DME, reflux | 42–52% |
| Acetonitrile, reflux | 58–65% |
| THF, reflux | 22% |
| Toluene, reflux | 60% |
| Heptane, reflux | 41% |
| isopropyl acetate, reflux | 22% |

Cyclization when Z=NHR: The cyclization can also be effected by treating amines with enamides (VI, Z=RNH) in the presence of a dehydrating agent such as POCl₃, as shown below. Nonlimiting examples of this cyclization is shown in Table 2.

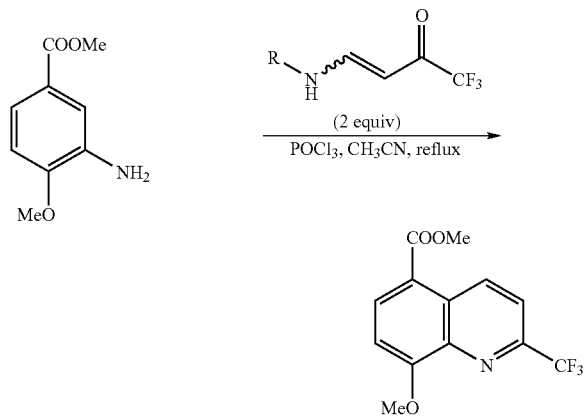

TABLE 2

| R | Yield |
|---|---|
| R = 2,4,6-tribromophenyl | 80% |
| R = 2,4,6-trichlorophenyl | 73% |
| R = 2,6-dimethylphenyl | 38% |
| R = 2,6-dichlorophenyl | 72% |
| R = t-butyl | 75% |

Example 3

Preparation of the Compound of Formula IX

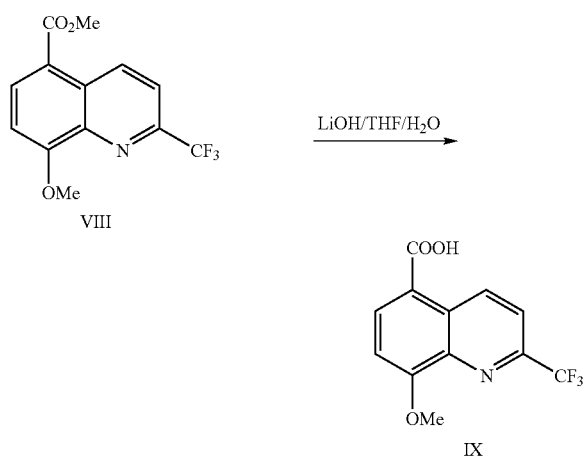

To a mixture of the quinoline VIII (600 g, 2.1 mol) in 4 L THF at room temperature, a solution of LiOH monohydrate (180 g, 4.3 mol) in 3 L of H₂O was added. After stirring at room temperature for 7 hours, the solvent THF was removed. EtOAc (12 L) was added followed by conc. HCl (330 mL). The layers were separated. The organic layer was dried over MgSO₄. Removal of solvent gave the desired acid IX, 8-methoxy-2-trifluoromethyl-5-quinolinecarboxylic acid, (560 g, 98% yield).

¹H NMR (400 MHz, DMSO) □ 4.09 (s, 3H), 7.39 (d, J=8.4 Hz, 1H), 8.11 (d, J=9.0 Hz, 1H), 8.45 (d, J=8.4 Hz, 1H), 9.71 (d, J=9.0 Hz, 1H), 13.25 (br, 1H).

Example 4

Preparation of the Compound of Formula X

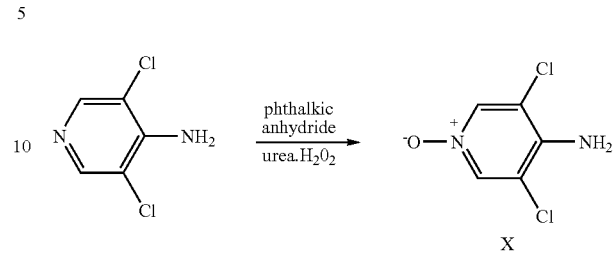

A mixture of phthalic anhydride (22.7 g, 2.5 eq) and urea hydrogen peroxide (17.3 g, 3.0 eq) in 80 mL 3:1 acetonitrile/methanol was heated at 35–40° C. until all solids dissolved. After cooling to room temperature, solid 4-amino-3,5-dichloropyridine (10 g, 61 mmol, available from Aldrich Chemical Company, Milwaukee, Wis.) was added portionwise. The reaction temperature was maintained at 20–25° C. during addition. This mixture was stirred at room temperature for 18 h and quenched with 150 mL chilled aqueous sodium sulfite solution (10.4 g Na₂SO₃, 1.4 eq). The resulting slurry was filtered and washed with water. The wet phthalate salt of the N-oxide was reslurried in 20 mL water and free based with aqueous K₂CO₃. After stirring for 6 h at room temperature, the slurry was filtered and washed with water. The wet cake was air-dried at 75° C. The residual water was removed by reslurrying the dry cake in refluxing methanol for 2 h. It was filtered at 10-20° C. and washed with methanol. The cake was vacuum dried at 75° C. until the methanol content was less than 0.1%. The product, 4 amino-3,5-dichloropyridine-N-oxide (the compound of formula X) was obtained (9.5 g, 98% purity, 85% yield).

¹H NMR (400 MHz, DMSO) δ 6.62 (s, 2H), 8.25 (s, 2H).

Example 5

Preparation of the Compound of Formula II

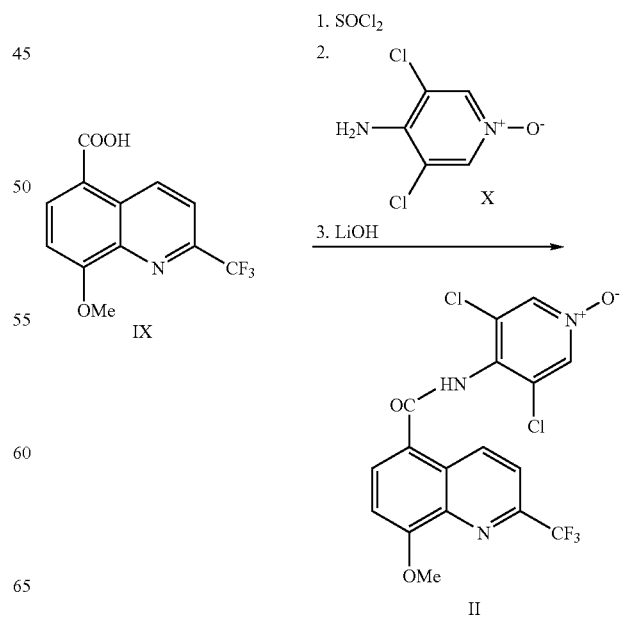

Preparation of the Acid Chloride of the Compound of Formula IX:

The acid (IX, 20 g, 74 mmol) was slurried in 100 mL dry acetonitrile. Thionyl chloride (9.2 g, 1.05 eq) was added at 40–45° C. in one portion. This mixture was heated at 40–45° C. for 1 h and the solution was used directly in the following coupling step.

Coupling Reaction:

The N-oxide (the compound of formula X) (26.4 g, 2 eq) and anhydrous lithium hydroxide powder (17.7 g, 10 eq) were mixed in 400 mL DMF. The mixture was stirred at room temperature for 1 h to give a creamy slurry. The warm acid chloride solution (40–45° C.) form above was added over 1 h while maintaining the batch temperature at 20–25° C. After stirring at room temperature for 1 h, the mixture was quenched by pouring it into a chilled dilute HCl solution. The pH was adjusted to be 0.5–1.5. The resulting slurry was stirred at room temperature for 1 h and filtered. The cake was washed with water and air dried at 55–60° C. to constant weight. A solid of the free base of Formula II was obtained as a hydrate, 28.9 g, 96% purity, 87% yield).

$^1$H NMR (400 MHz, DMSO) δ 3.97 (s, 3H), 7.34 (d, J=8.4 Hz, 1H), 7.98 (d, J=8.8 Hz, 1H), 8.05 (d, J=8.4 Hz, 1H), 8.62 (s, 2H), 9.00 (d, J=8.8 Hz, 1H), 10.70 (br s, 1H).

Optional Purification of the Compound of Formula II Via Acetic Acid Complex:

The solid obtained in the coupling reaction described above was purified as follows:

Preparation of the Acetic Acid Complex of the Compound of Formula II:

The above crude product (150 g) was dissolved in 9:1 acetic acid/water mixture (3 L) at 100° C. The solution was cooled over 2 h to room temperature and filtered. The cake was washed with 9:1 acetic acid/water mixture (600 mL) and dried at 55° C. in an air draft oven. The acetic acid complex of compound of Formula II was obtained as an off-white solid (141.5 g, 76% yield).

$^1$H NMR (400 MHz, DMSO) δ 1.91 (s, 3H), 4.11 (s, 3H), 7.49 (d, J=8.3 Hz, 1H), 8.13 (d, J=9.0 Hz, 1H), 8.20 (d, J=8.2 Hz, 1H), 8.77 (s, 2H), 9.14 (d, J=8.8 Hz, 1H), 10.78 (br s, 1H), 11.97 (br s, 1H).

Preparation of the Compound of Formula II:

The acetic acid complex of the compound of formula II (27 g) was mixed with 0.3 g micronized Form 2 seeds (prepared in-house) in 540 mL isopropanol. The slurry was heated at reflux for 1 h. It was cooled to 20–25° C. over 1 h. After being stirred at room temperature for another 30 min, it was filtered and washed with isopropanol. The cake was vacuum dried at 55–60° C. to constant weight (23.3 g, 98% recovery). The NMR data is given above.

It will be understood that various modifications can be made to the embodiments and examples disclosed herein. Therefore, the above description should not be construed as limiting, but merely as exemplifications of preferred embodiments. Those skilled in the art will envision various modifications within the scope and spirit of the claims appended hereto.

What is claimed is:

1. A process of making a compound of formula IV comprising:

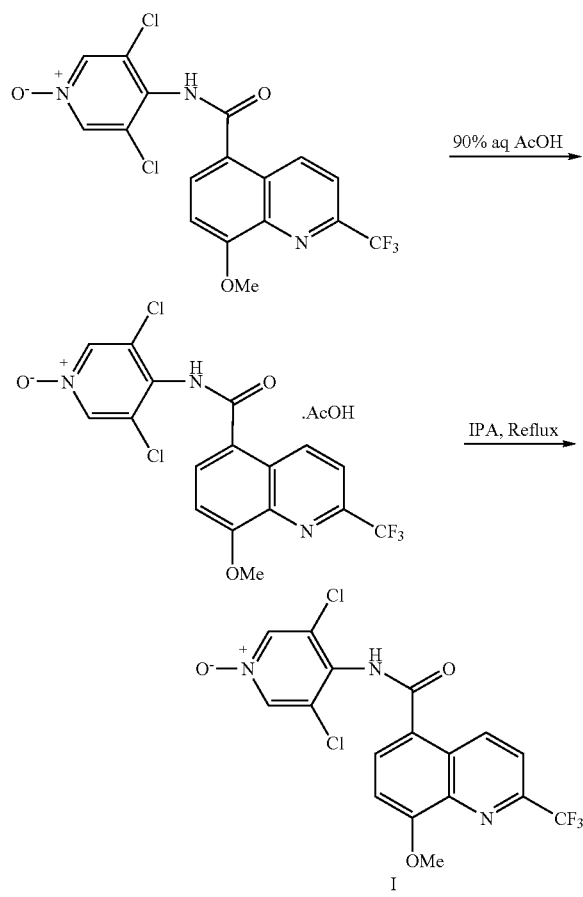

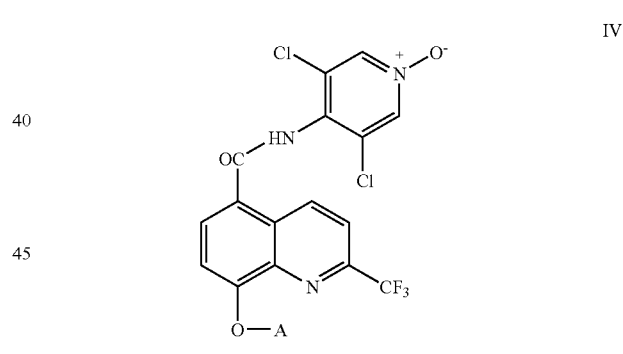

(1) reacting a compound of formula V with a compound of formula VI to yield a compound of formula VII:

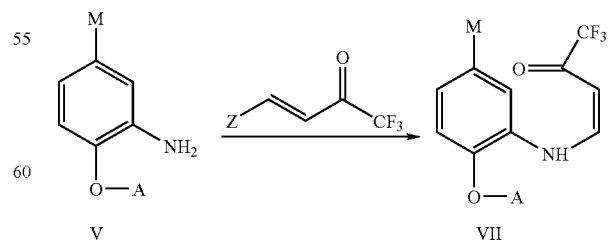

wherein A is selected from the group consisting of H, alkyl, cycloalkyl, heterocyclyl, —CF$_3$, aryl, and heteroaryl;

M is selected from the group consisting of Br, Cl, I, —CN, —C(O)OR, —C(O)NR$^1$R$^2$, and —C(O)SR$^3$;

Z is selected from the group consisting of halogen, —OR$^4$, —NR$^5$R$^6$ and —SR$^7$;

R is selected from the group consisting of H, alkyl, aryl, aralkyl, heteroaryl, cycloalkyl, and heterocyclyl; and R$^1$, R$^2$, R$^3$, R$^4$, R$^5$, R$^6$, and R$^7$, which can be the same or different, are each independently selected from the group consisting of H, alkyl, aryl, aralkyl, heteroaryl, cycloalkyl, and heterocyclyl, wherein said alkyl, aryl, aralkyl, heteroaryl, cycloalkyl, and heterocyclyl can each be unsubstituted or substituted with 1–4 independently selected W moieties, which can be the same or different, wherein W is selected from the group consisting of alkyl, halo, cycloalkyl, heterocyclyl, aryl and heteroaryl;

(2) cyclizing the compound of formula VII to yield a compound of formula VIII:

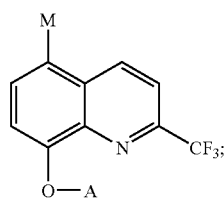

(3) converting the compound of formula VIII to yield a compound of formula IX:

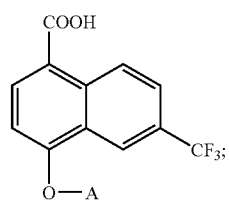

and (4) reacting the compound of formula IX with a compound of formula X to yield the compound of formula IV:

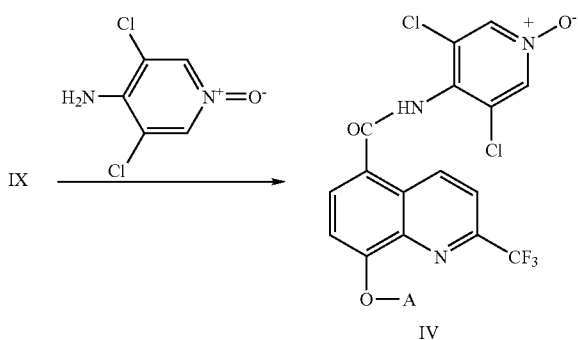

2. The process according to claim 1, wherein M is methoxycarbonyl, A is methyl and Z is ethoxy.

3. The process of claim 2, wherein step 1 is conducted in an alcohol solvent at about −20° C. to about the reflux temperature of the solvent and for about 30 minutes to until the reaction is complete.

4. The process according to claim 2, wherein said cyclizing in step 2 comprises adding to the compound of formula VII a dehydrating agent selected from the group consisting of POCl$_3$, PCl$_3$, Tf$_2$O, Ms$_2$O, PCl$_5$ and P$_2$O$_5$ in a solvent, at about room temperature to about the reflux temperature of said solvent, for about 30 minutes to until the reaction is complete.

5. The process according to claim 4, wherein the dehydrating agent is POCl$_3$.

6. The process of claim 4, wherein said solvent is selected from the group consisting of ether, hydrocarbon, nitrile, ester, chlorinated solvents and mixtures thereof.

7. The process of claim 6, wherein said solvent is acetonitrile.

8. The process of claim 2, wherein step 3 comprises treating the compound of formula VIII with a base selected from the group consisting of sodium carbonate, potassium carbonate, sodium bicarbonate, potassium bicarbonate, sodium hydroxide, potassium hydroxide, and lithium hydroxide and the like, and mixtures thereof, in solvent selected from the group consisting of an ether, alcohol, nitrile and the like, and mixtures thereof, about room temperature to about the reflux temperature, for about 2 hours or until the reaction is complete, to yield the compound of formula IX.

9. The process of claim 8, wherein said base is lithium hydroxide and said solvent is tetrahydrofuran.

10. The process according to claim 2, wherein step 4 comprises first converting the compound of formula IX into its acid chloride, followed by reacting said acid chloride with the compound of formula X in the presence of a base in a solvent at about 10° C. to about 80° C., for about 30 minutes to about the completion of the reaction, followed by acidification to yield the compound of formula IV.

11. The process of claim 10, wherein said acid chloride is formed by the reacting the compound of formula IX with SOCl$_2$ or oxalyl chloride.

12. The process according to claim 11, wherein said acid chloride is SOCl$_2$.

13. The process of claim 10, wherein said base is selected from the group consisting of sodium hydride, sodium methoxide, potassium methoxide, sodium carbonate, potassium carbonate, sodium hydride, sodium bicarbonate, potassium bicarbonate, sodium hydroxide, potassium hydroxide, lithium hydroxide, and the like, and mixtures thereof.

14. The process of claim 13, wherein said base is lithium hydroxide.

15. The process of claim 10, wherein said solvent is selected from the group consisting of nitrile, hydrocarbon, chlorinated hydrocarbon, amide, ether, and the like and mixtures thereof.

16. The process of claim 15, wherein said solvent is acetonitrile, DMF or mixtures thereof.

17. The process of claim 10, wherein said acid is selected from the group consisting of acetic acid, HCl, H$_2$SO$_4$, and mixtures thereof.

18. The process of claim 17, wherein said acid is HCl.

19. A process to prepare a compound of the formula:

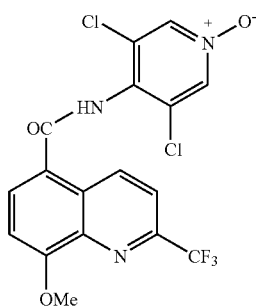

said process comprising:

(1) reacting a compound of formula V with a compound of formula VI to yield a compound of formula VII, in an alcohol solvent at about −20° C. to about the reflux temperature of the solvent and for about 30 minutes to until the reaction is complete:

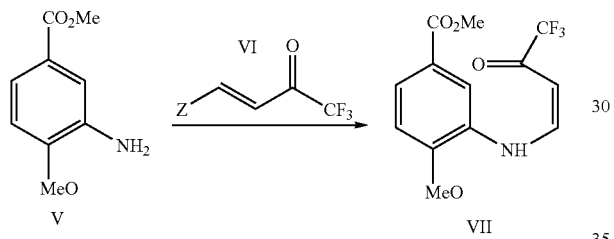

(2) cyclizing the compound of formula VII to yield a compound of formula VIII, by treating the compound of formula VII in a solvent with a dehydrating agent selected from the group consisting of $POCl_3$, $PCl_3$, $Tf_2O$, $Ms_2O$, $PCl_5$ and $P_2O_5$, at about room temperature to about the reflux temperature of said solvent, for about 30 minutes to until the reaction is complete:

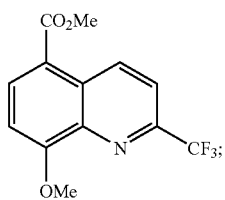

(3) hydrolyzing the compound of formula VIII to yield a compound of formula IX, by treating the compound of formula VIII with a base selected from the group consisting of sodium carbonate, potassium carbonate, sodium bicarbonate, potassium bicarbonate, sodium hydroxide, potassium hydroxide, and lithium hydroxide and mixtures thereof, in solvent selected from the group consisting of an ether, alcohol, nitrile and the like, and mixtures thereof, about room temperature to about the reflux temperature, for about 2 hours or until the reaction is complete:

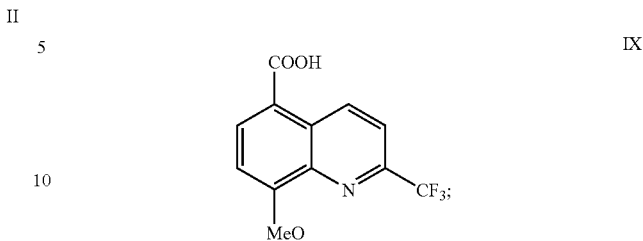

and (4) reacting the compound of formula IX with a compound of formula X to yield the compound of formula II, with said reaction comprising first converting the compound of formula IX into its acid chloride, followed by reacting said acid chloride with the compound of formula X in the presence of a base in a solvent at about 10° C. to about 80° C., for about 30 minutes to about the completion of the reaction, followed by acidification to yield the compound of formula II:

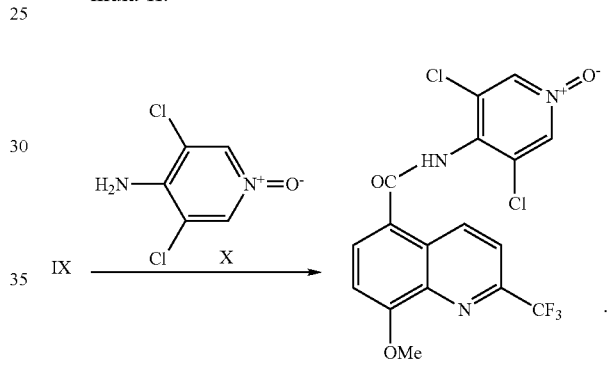

20. A compound of the formula:

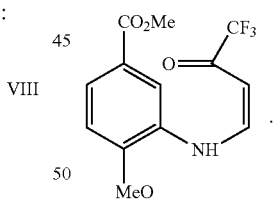

21. A compound of the formula:

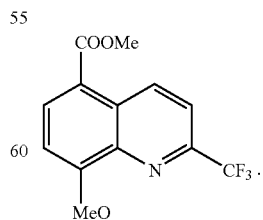

* * * * *